United States Patent [19]

Buican et al.

[11] Patent Number: 5,100,627

[45] Date of Patent: Mar. 31, 1992

[54] CHAMBER FOR THE OPTICAL MANIPULATION OF MICROSCOPIC PARTICLES

[75] Inventors: Tudor N. Buican; Bryan D. Upham, both of Los Alamos, N. Mex.

[73] Assignee: The Regents of the University of California, Oakland, Calif.

[21] Appl. No.: 443,287

[22] Filed: Nov. 30, 1989

[51] Int. Cl.$^5$ .................... G01N 21/00; G01N 31/01; G02B 00/00
[52] U.S. Cl. ........................... 422/108; 422/58; 422/68.1; 422/82.05; 356/244; 359/350
[58] Field of Search ............ 422/58, 82.05, 68.1, 422/108; 435/300, 301; 350/536, 1.1

[56] References Cited

U.S. PATENT DOCUMENTS

| | | | |
|---|---|---|---|
| 3,808,550 | 4/1974 | Askin | 372/94 |
| 3,899,296 | 8/1975 | Mailen et al. | 422/72 |
| 4,279,862 | 7/1981 | Bretaudiere et al. | 422/72 |
| 4,284,602 | 8/1981 | Kelton et al. | 422/72 |
| 4,661,913 | 4/1987 | Wu et al. | 422/82.05 |
| 4,673,288 | 6/1987 | Thomas et al. | 356/246 |
| 4,818,103 | 4/1989 | Thomas et al. | 356/246 |
| 4,893,886 | 1/1990 | Askin et al. | 350/1.1 |
| 4,979,822 | 12/1990 | Sommer | 356/246 |
| 4,983,038 | 1/1991 | Ohki et al. | 356/246 |

OTHER PUBLICATIONS

Ashkin et al., "Optical Trapping and Manipulation of Viruses and Bacteria", Science, vol. 235, 3/20/87, pp. 1517-1520.

Ashkin et al., "Optical Trapping and Manipulation of Single Cells Using Infrared Laser Beams"; Nature, vol. 330, 24/31, 12/1987, pp. 769-771.

Buiran et al., "New Technilogies in Cytometry", Proceedings of SPIE, vol. 1063, 1989, pp. 189-197.

Primary Examiner—Robert J. Warden
Assistant Examiner—Theresa A. Trembley
Attorney, Agent, or Firm—Ray G. Wilson

[57] ABSTRACT

A particle control chamber enables experiments to be carried out on biological cells and the like using a laser system to trap and manipulate the particles. A manipulation chamber provides a plurality of inlet and outlet ports for the particles and for fluids used to control or to contact the particles. A central manipulation area is optically accessible by the laser and includes first enlarged volumes for containing a selected number of particles for experimentation. A number of first enlarged volumes are connected by flow channels through second enlarged volumes. The second enlarged volumes act as bubble valves for controlling the interconnections between the first enlarged volumes. Electrode surfaces may be applied above the first enlarged volumes to enable experimentation using the application of electric fields within the first enlarged volumes. A variety of chemical and environmental conditions may be established within individual first enlarged volumes to enable experimental conditions for small scale cellular interactions.

20 Claims, 4 Drawing Sheets

CHAMBER FOR THE OPTICAL MANIPULATION OF MICROSCOPIC PARTICLES

This invention is the result of a contract with the Department of Energy (Contract No. W-7405-ENG-36).

BACKGROUND OF INVENTION

This invention relates to optical trapping and, more particularly, to the optical trapping of microscopic particles, such as biological cells, for manipulation and experimentation.

A laser beam can interact with microscopic particles to produce radial forces on a particle to trap the particle on the beam axis. These optical traps have been found effective for trapping biological particles, i.e., bacteria, viruses, cells, etc., for experimental manipulation. See A. Ashkin et al., "Optical Trapping and Manipulation of Single Cells Using Infrared Laser Beams," 330 Nature, pp 769-771 (December 1987), incorporated herein by reference. Infrared laser beams with sufficient power to move the biological particles through a surrounding medium do not appear to interfere with normal biological functions. A sample cell is provided with a hollow glass fiber for use in separating and removing selected particles from the sample cell. However, the fiber containing the selected cells must be physically removed from the sample cells for further experimentation.

In another application of optical trapping, a stream of particles is formed in a laser beam and transported through an interrogation chamber for selecting particles with predetermined properties. When a particle is identified with the desired property, a second laser beam acts to remove the particle from the transport beam for removal and subsequent experimental use. See U.S. patent application Ser. No. 07/126,156, filed Nov. 30, 1987, for "Laser Particle Sorter," now U.S. Pat. No. 4,887,721, issued Dec. 19, 1989, incorporated herein by reference.

It would be desirable to provide for experimentation on biological cells in a controlled and contained environment that can be suitably isolated from environmental contamination. Accordingly, it as an object of the present invention to provide a chamber that is suitable for biological particle optical manipulation and experimentation.

Another object of the present invention is to provide for introducing particles into a controlled environment for biological experiments.

Yet another object is to provide for optically introducing a plurality of biological particles into controlled compartments which can be selectively interconnected.

One other object is to provide a chamber with compartments that are connected for the introduction and circulation of cell and chromosome suspensions, culture media, and reagents.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the apparatus of this invention may comprise a particle control chamber for use with a laser system for trapping and manipulating the particles. A manipulation chamber has a central section defining a plurality of inlet and outlet ports for the particles and for fluids used to control or to contact the particles. A plurality of flow channels connects the inlet and outlet ports and defines a manipulation area in the central section which is optically accessible by the laser system and an imaging system. The manipulation area further includes a first enlarged volume in selected first ones of the channels usable for introducing the particles, each said first volume being effective to contain a selected number of particles, and interconnection channels for selectively interconnecting the first enlarged volumes. In one particular embodiment, a second enlarged volume may be included in second ones of the channels usable for controlling a distribution of the particles and the fluids in the manipulation area, each said second volume being effective for trapping a flow control air bubble.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION OF THE DRAWINGS

In accordance with the present invention, a particle manipulation chamber cooperates with a laser system for trapping microscopic particles. The manipulation chamber enables selected particles to be introduced into the chamber, selectively combined with other particles, and placed in a controlled environment, i.e., temperature, culture medium, reagents, etc., for conducting experiments. A disposable central section assembly provides a sterile environment for each experiment with no cross-contamination. An optical viewing system permits an operator to manipulate particles within the system and to view the progress of experiments within the chamber. As herein described, the manipulation chamber has the following functional characteristics:

1. Multiple compartments permit particles, e.g. biological particles (i.e. cells and chromosomes), to be separated and/or combined for microexperiments;
2. The compartments are connected by channels having dimensions which are large enough to manipulate particles, but small enough to substantially preclude particle drifting;
3. The compartments are connected to external ports to allow the introduction and circulation of experimental fluids, e.g. cell and chromosome suspensions, culture media, and reagents;
4. The chamber is enclosed by optical windows of a quality effective to permit particle trapping and imaging at the selected wavelengths;
5. The chamber compartments and channels are shallow to allow concentrated samples to be processed and analyzed;
6. The chamber design provides efficient heat transfer between the compartments and external temperature control devices.

Figure 1:
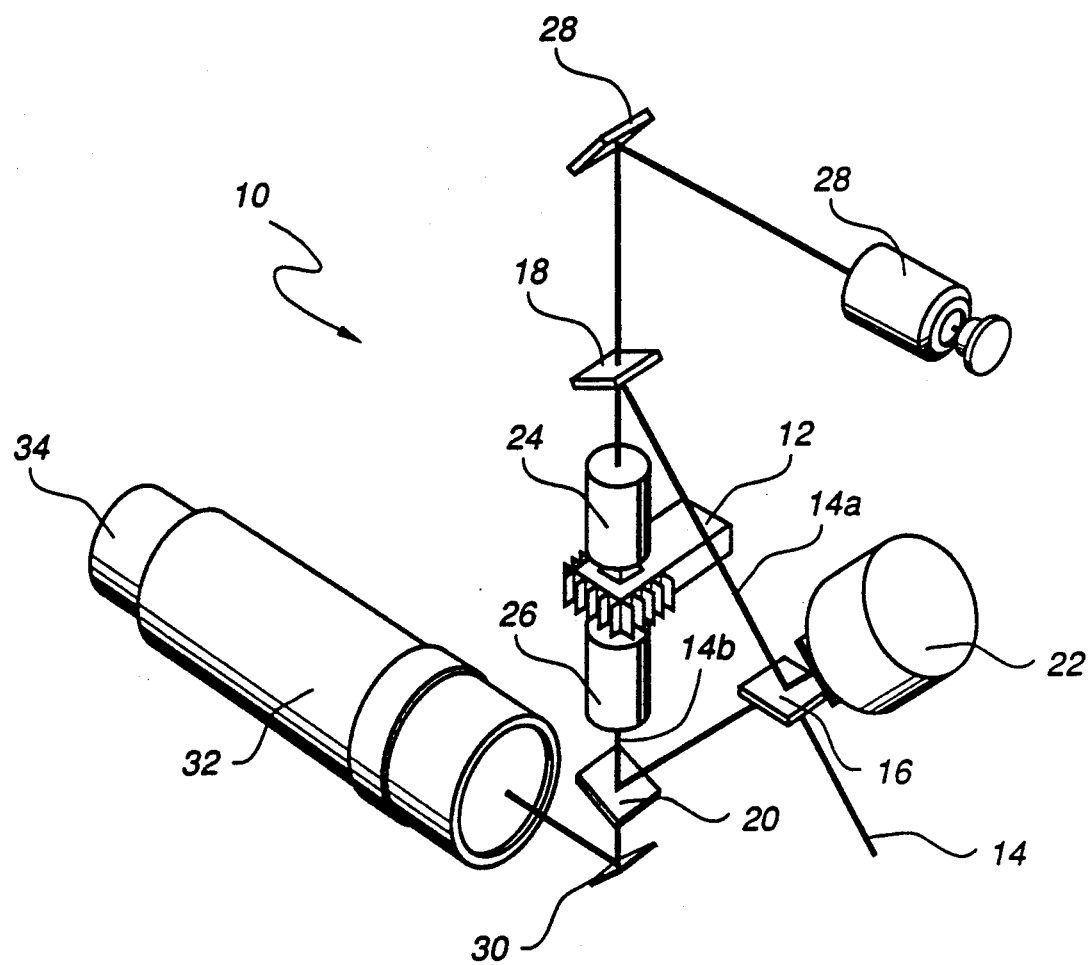
FIG. 1 is a pictorial illustration of a laser system according to the present invention.

Referring now to FIG. 1, there is shown a laser and optics system 10 in accordance with one embodiment of the present invention. Manipulation chamber 12, hereinafter discussed for FIGS. 2-7, has trapping laser beams 14a, 14b from laser beam 14, split by beam splitter 16 and directed by dichroic mirrors 18, 20 through chamber 12. Alignment camera 22 observes a portion of the beams in the optical loop to maintain the two beams in coaxial alignment and for adjusting the distance between the two beam waists formed by microscope objectives 24, 26 for trapping particles in chamber 12. An imaging system formed of an illumination source 28, mirrors 28, 30, zoom lens 32, and imaging camera 34 enable a video display to be formed for the operator to direct particle movement within chamber 12 and to observe the progress of the microexperiments.

It will be appreciated that laser beam 14 is stationary in the preferred embodiment and manipulation chamber 12 is positioned to effect the relative movement of particles trapped by beams 14a, 14b within chamber 12. Thus, the laser optics are simplified and large relative movements of the particles within chamber 12 can be obtained.

Manipulation chamber 12 is comprised of a central channel section 42 (FIG. 2), upper window 92 (FIG. 4), a lower window (not shown), inner holder 110 (FIGS. 5 and 6), and an outer shell 140 (FIG. 7). Central channel section 42 is sandwiched between upper window 92, which may provide structural support and external ports for particle and fluid access, and a lower window for sealing. The resulting assembly is mounted in holder 110 for clamping the assembly, including central section 42, providing temperature sensor access 116, and providing a piezoelectric crystal 128 for dislodging particles within central section 42. An outer shell 140 connects to the positioning stage and pumps heat between the chamber and the surrounding environment.

Figure 2:
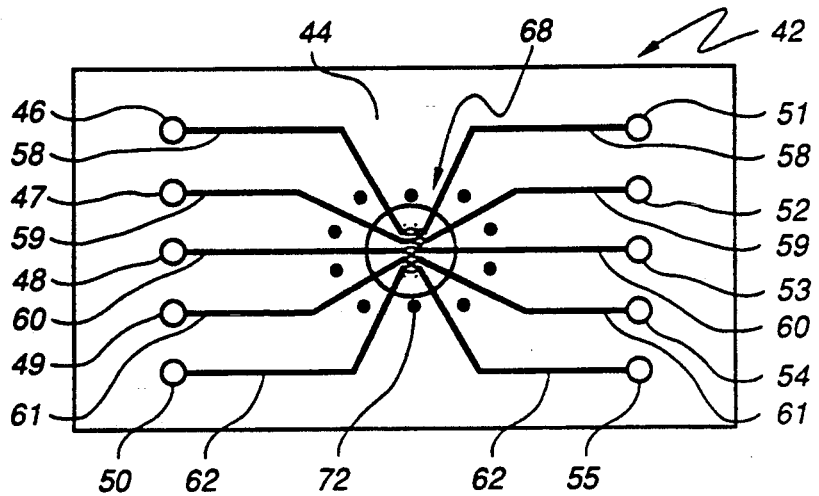
FIG. 2 is a plan view of a central flow section.

Central channel section 42, depicted in FIG. 2, is a sheet 44 of material that defines manipulation compartments 74-78, interconnecting channels 82-86, process flow channels 58-62, and external ports 46-55. The number and configuration of compartments and channels is exemplary only, and is not intended to limit the scope of this invention. Sheet 44 may be formed from stainless steel shim stock and machined with a suitable laser beam, or may be formed from ceramic sheet which is photoetched to produce the desired flow configurations. Photoetching permits more precise machining to be done but the ceramic stock can only be lapped to a thickness of about 250 micrometers, while the stainless steel shim stock can be obtained with a thickness of about 100 micrometers. Sheet 44 further defines connection holes 72 (ten places) for glue injection close to manipulation area 68 and fiducial marks 88 for calibrating the optical manipulator video and position control systems.

Figure 3:
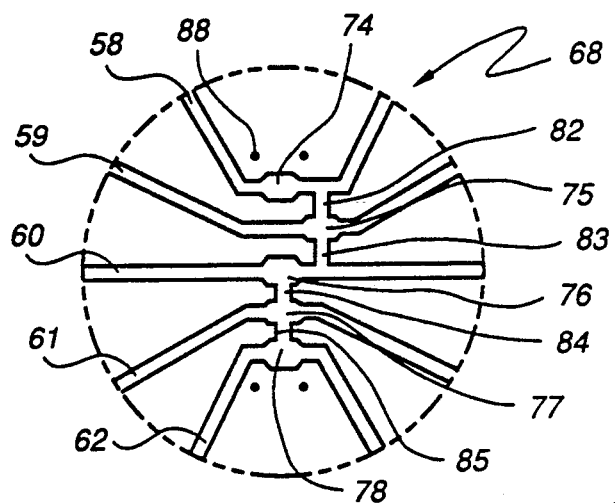
FIG. 3 is an enlarged view of a manipulation area on the flow sheet shown in FIG. 2.

Process flow channels 58-62 enable various particles and fluids to be injected and removed through selected external ports 46-55. As shown in FIG. 3, particles are maneuvered in manipulation area 68 through flow channels 58, 60, 62 into manipulation compartments 74, 76, 78, respectively. Compartments 74, 76, 78 define volumes suitable for microexperiments containing a selected number of particles or for introducing test fluids, e.g. culture media or reagents, adjacent the particles to be tested. Connections between experimental compartments is controlled through interconnection channels 82-85 by the use of valve compartments 75, 77 which may be bubble valves operated by the introduction of a suitable fluid through channels 59, 61, respectively, using positive displacement pumps or syringes. Exemplary dimensions are shown in Table A.

TABLE A

| | |
|---|---|
| Process Flow Channels 58-62 | 0.114 mm wide |
| Manipulation Compartment 74, 76, 78 | 0.305 mm × 0.305 mm |
| Valve Compartment 75, 77 | 0.200 mm × 0.200 mm |
| External Ports 46-55 | 1.02 mm dia. |

Figure 3A:
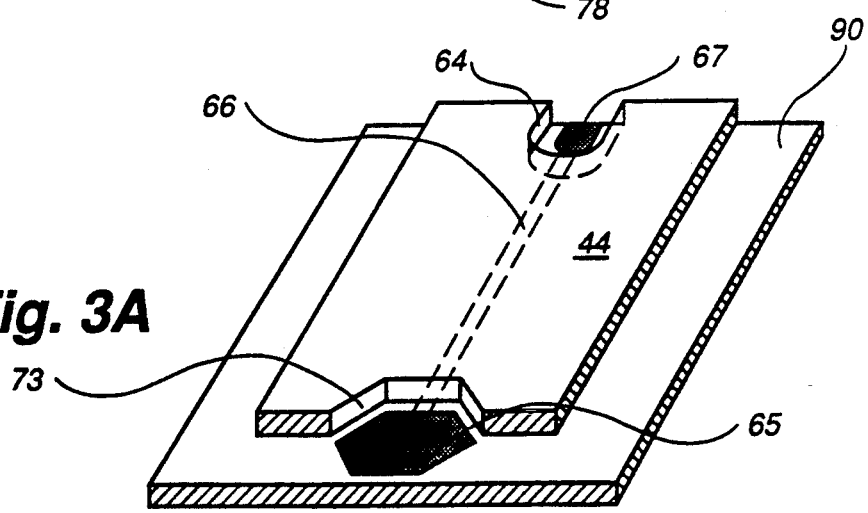
FIG. 3A is a schematic in partial cross section of electroded chambers in the manipulation area of FIG. 3.

In one embodiment, the window cover sheets for central section 42 may include electrode surfaces for applying an electric field within one or more of the manipulation compartments 74, 76, and 78 for use in experimental techniques, such as cell electrofusion and electroporation. One possible electrode configuration is schematically shown in partial cross section in FIG. 3A. Electrode area 65 is formed on window 90 within an area defined by manipulation chamber 73 formed in flow sheet 44. Connecting electrode pad 67 is also formed along an edge of window 90 and is connected through conducting strip 66 with electrode area 65. An edge notch 64 is formed in flow sheet 44 for connecting pad 67 with external circuitry.

It will be appreciated that flow sheet 44 is formed of an insulating material, such as ceramic, for use with electroded surfaces on window 90. Electroded surfaces 65, 66, and 67 are conventionally formed, e.g. by vacuum deposition and photolithography techniques, and are preferably of a transparent material, such as gold or platinum, in the required thickness. Electrode surfaces may be formed on either one or both of the window surfaces covering any given manipulation chamber 73 and connecting pads 67 formed at any convenient location about the perimeter of manipulation chamber 12 (FIG. 1).

Figure 4:
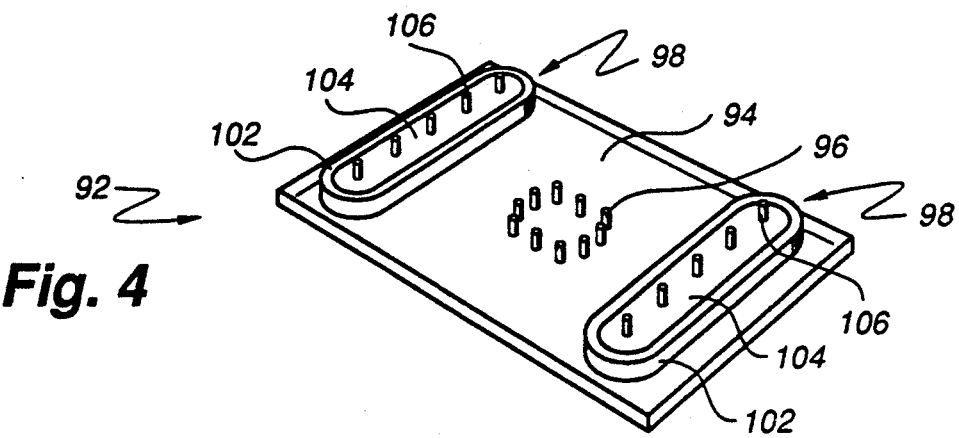
FIG. 4 is an isometric view of one window for covering a side of the flow sheet shown in FIG. 2.

An isometric view of an upper window for covering central flow sheet 44 is shown in isometric view in FIG. 4. Upper window 92 serves as a structural support for central channel section 42 while providing optical access to sheet 42 for imaging and optical trapping. The embodiment shown in FIG. 4 includes holes 96 for introducing glue for attaching window 92 to sheet 42. Window 92 includes external port assemblies 98 having connectors 106 (ten places as shown) in registry with external ports 46-55 in channel section 42. Connectors 106 may be formed from hypodermic needles which are held in place by a sealant 104, such as epoxy, contained in wells 102. The embodiment for use with a stainless steel flow sheet 42 is substantially identical, but may omit holes 96. A lower window (not shown) seals the side of flow sheet 42 opposite upper window 92. Thin coverslips of 170 μm thickness for the lower window are available from Corning Glass Company.

Figure 5:
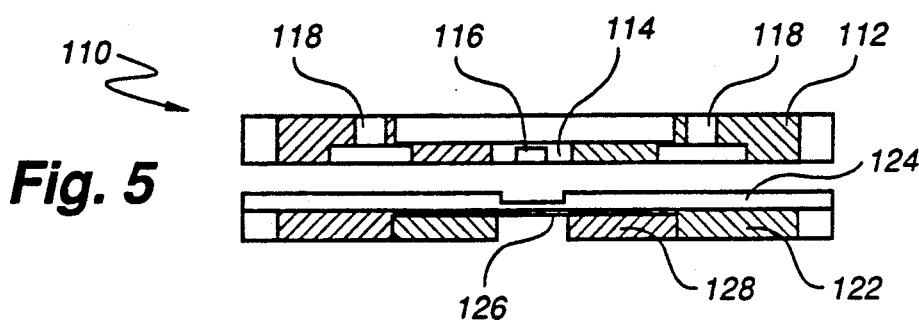
FIG. 5 is a cross section of an inner holder for supporting the flow sheet shown in FIG. 2.

An inner holder 110 is depicted in FIG. 5 for contacting the optical manipulation chamber formed from central flow sheet section 42, upper window 92 and a lower window (not shown). Inner holder 110 clamps the optical manipulation chamber to enable effective heat transfer between the chamber and a surrounding outer shell (FIG. 7) to permit the application of mechanical shocks to the optical chamber to dislodge particles which may tend to adhere to the chamber walls, and to enable the optical chamber to be attached to a mechanical positioning system for relative movement of particles within the optical chamber.

Inner holder 110 includes an upper holder 112 and lower holder 122, both of a material having a high heat transfer coefficient, such as brass. Upper holder 112 defines external port access cavities 118 for port connections 106 (FIG. 4) and optical access port 114 for laser access to manipulation area 68 within central section 42, and includes one or more temperature sensors 116 for use in controlling the temperature within central section 42. Lower holder 122 defines optical chamber cavity 124 and optical access port 126, and includes piezoelectric element 128 for transmitting short mechanical shocks to within the optical chamber.

Figure 6:
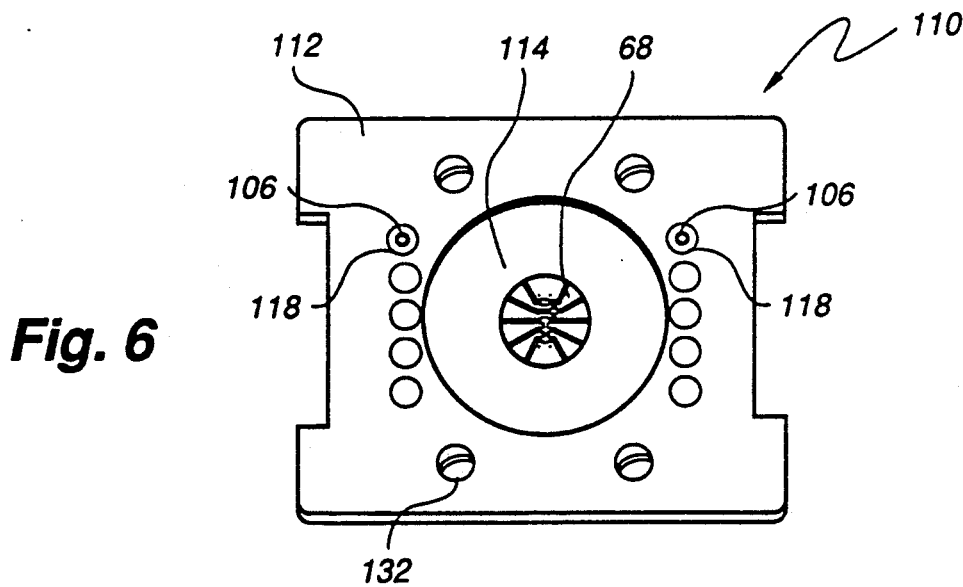
FIG. 6 is a pictorial illustration of an assembled inner holder and central flow sheet assembly.

An assembled inner holder 110 is depicted in FIG. 6. Upper holder 112 is secured to lower holder 122 (not shown) by a clamping device, such as bolts 132. Access to the external port connections 106 is provided through access holes 118. Optical access to at least manipulation area 68 on central flow sheet 42 is obtained through optical access port 114.

Figure 7A:
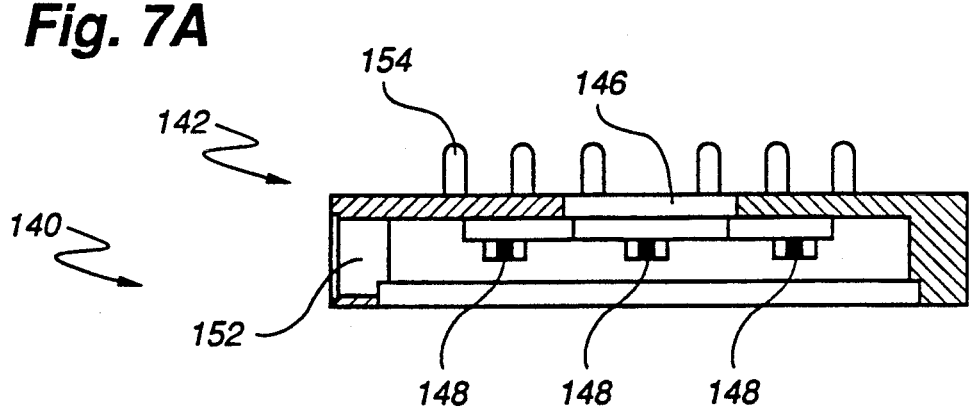
FIGS. 7A and 7B are cross section views of the outer shell components for thermally controlling the inner holder and central flow sheet assembly shown in FIG. 6.
Figure 7B:
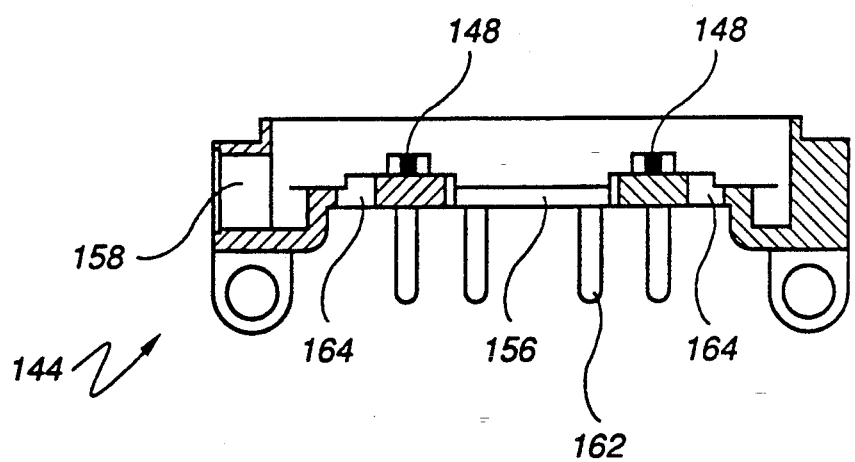

Outer shell 140 for connecting inner holder 110 to a positioning device and for pumping heat between central section 42 and the environment is shown in FIGS. 7A and 7B in cross-sectional view. Upper shell 142 defines optical access port 146 and electrical connector cavity 152 and includes a plurality of thermoelectric elements 148. Lower shell 144 defines optical access port 156, external port access openings 164, and electrical connector cavity 158, and includes a second plurality of thermoelectric elements 148. Heat transfer fins 154 and 162 depend from outer shell 142 and inner shell 144, respectively, to facilitate temperature control. Thermoelectric elements 148 thermally contact inner holder 110 for controlling the temperature within manipulation area 68 in central flow section 42 (FIG. 2) as determined by temperature sensors 116 within upper holder 112 (FIG. 5). Suitable thermoelectric elements require a maximum of 0.8 amps per element at 2.8 volts to provide a maximum heat transfer through each element of 0.95 watts.

Thus, the manipulation chamber assembly 12 (FIG. 1) described above provides a microlaboratory for conducting experiments on microscopic particles. The multiple compartments in manipulation area 68 of central flow section 42 are the microscopic equivalent of test tubes between which particles can be optically transferred. Interconnecting channels 82-85 and valve compartments 75, 77 allow the composition of materials in the compartments to be selectively modified for controlled experiments. A variety of biological particles have been optically trapped and manipulated within chamber 12, including mammalian cells (mouse thymocytes, spleen cells; and cultured fibroblasts, rat erythrocytes and alveolar macrophages, and human erythrocytes), plant protoplasts, and CHO chromosomes. A trapping laser power of 15 mW was used without any observed damage to the particles.

It will be understood that inner holder 110 and outer holder 140 can be formed as an integrated unit and still provide the requisite functions of temperature control and particle dislodgement. As described, the separate units provide easy fabrication and assembly, as well as access for possible maintenance on thermoelectric elements 148.

The foregoing description of the preferred embodiments of the invention have been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. In a laser system for optically trapping and manipulating microscopic particles with the use of a particle control chamber the improvement comprising:
   a manipulation chamber having a central section defining a plurality of inlet and outlet ports for introducing fluids and said particles within said chamber, a plurality of flow channels connecting said inlet and outlet ports, and a manipulation area optically accessible by said laser system;
   said manipulation area further including a first enlarged volume in selected first ones of said flow channels usable for introducing said particles, each said first volume being effective to contain a selected number of said particles and interconnection channels for selectively interconnecting said first enlarged volumes.

2. A laser system according to claim 1, wherein said manipulation chamber further includes window means for sealing said central section while enabling optical access to at least said manipulation area.

3. A laser system according to claim 2, wherein said window means further includes connector means in sealing registration with said inlet and outlet ports for introducing said particles and fluids within said flow channels.

4. A laser system according to claim 2, wherein said window means further includes electrode means operatively associated with said first enlarged volume for establishing an electric field within said first enlarged volume.

5. A laser system according to claim 1, further including holder means for receiving and supporting said manipulation chamber while maintaining optical access to at least said manipulation area.

6. A laser system according to claim 5, wherein said holder further includes means for supporting a piezoelectric transducer in proximity to said manipulation chamber effective for transmitting a generated shock from said piezoelectric transducer to said manipulation chamber.

7. A laser system according to claim 5, further including temperature sensor means, wherein said holder contacts said manipulation chamber with a heat transfer surface having a heat transfer coefficient effective for temperature control of said manipulation chamber and defines access for said temperature sensor means to contact said manipulation chamber.

8. A laser system according to claim 5, further including temperature control means effective for heat transfer between said manipulation chamber and an outside environment.

9. A laser system according to claim 8, wherein said temperature control means includes thermoelectric elements for contacting said heat transfer surface to pump heat between said holder and said environment.

10. A laser system according to claim 9, wherein said temperature control means includes depending heat exchange fins for heat transfer between said thermoelectric elements and said environment.

11. In a laser system for optically trapping and manipulating microscopic particles with the use of a particle control chamber the improvement comprising:

a manipulation chamber having a central section defining a plurality of inlet and outlet ports for introducing fluids and said particles within said chamber, a plurality of flow channels connecting said inlet and outlet ports, and a manipulation area optically accessible by said laser system;

said manipulation area further including a first enlarged volume in selected first ones of said flow channels usable for introducing said particles, each said first volume being effective to contain a selected number of said particles, a second enlarged volume in selected second ones of said flow channels usable for controlling the distribution of said particles and said fluids in said manipulation area, each said second volume being effective for trapping a flow control air bubble, and interconnection channels for selectively interconnecting said first enlarged volumes through said second enlarged volumes.

12. A laser system according to claim 11, wherein said manipulation chamber further includes window means for sealing said central section while enabling optical access to at least said manipulation area.

13. A laser system according to claim 12, wherein said window means further includes electrode means operatively associated with said first enlarged volume for establishing an electric field within said first enlarged volume.

14. A laser system according to claim 12, wherein said window means further includes connector means in sealing registration with said inlet and outlet ports for introducing said particles and fluids within said flow channels.

15. A laser system according to claim 11, further including holder means for receiving and supporting said manipulation chamber while maintaining optical access to at least said manipulation area.

16. A laser system according to claim 15, wherein said holder further includes means for supporting a piezoelectric transducer in proximity to said manipulation chamber effective for transmitting a generated shock from said piezoelectric transducer to said manipulation chamber.

17. A laser system according to claim 15, further including temperature sensor means, wherein said holder contacts said manipulation chamber with a heat transfer surface having a heat transfer coefficient effective for temperature control of said manipulation chamber and defines access for said temperature sensor means to contact said manipulation chamber.

18. A laser system according to claim 15, further including temperature control means effective for heat transfer between said manipulation chamber and an outside environment.

19. A laser system according to claim 18, wherein said temperature control means includes thermoelectric elements for contacting said heat transfer surface to pump heat between said inner holder and said environment.

20. A laser system according to claim 19, wherein said temperature control means includes depending heat exchange fins for heat transfer between said thermoelectric elements and said environment.

* * * * *